(12) United States Patent
Billingsley

(10) Patent No.: US 6,309,222 B1
(45) Date of Patent: Oct. 30, 2001

(54) DENTAL CONTAINMENT DEVICE

(76) Inventor: Cheryl B. Billingsley, 2423 Old Coach La., Richmond, VA (US) 23233

( * ) Notice: Subject to any disclaimer, the term of this patent is extended or adjusted under 35 U.S.C. 154(b) by 0 days.

(21) Appl. No.: 09/452,521

(22) Filed: Dec. 1, 1999

(51) Int. Cl.$^7$ ................................................ A61C 5/00
(52) U.S. Cl. .................................... 433/229; 132/73
(58) Field of Search ...................... 433/229, 49; 132/73, 132/73.5; 312/209

(56) References Cited

U.S. PATENT DOCUMENTS

| | | |
|---|---|---|
| 4,059,903 | 11/1977 | Piet et al. . |
| 4,108,509 | 8/1978 | Piet et al. . |
| 4,505,190 | 3/1985 | Fink et al. . |
| 4,949,738 | 8/1990 | Hubbard . |
| 4,956,915 * | 9/1990 | Anderson .............................. 132/73.5 |
| 5,046,606 * | 9/1991 | Morelli ................................. 132/73.5 |
| 5,350,064 * | 9/1994 | Schneck ................................ 206/368 |
| 5,462,434 | 10/1995 | Mahr . |
| 5,464,029 | 11/1995 | Rentz . |
| 5,928,075 * | 7/1999 | Miya et al. ............................ 312/209 |

FOREIGN PATENT DOCUMENTS

276638 * 8/1988 (EP) ........................................ 433/40

* cited by examiner

Primary Examiner—Todd E. Manahan
(74) Attorney, Agent, or Firm—Greenblum & Bernstein, P.L.C.

(57) ABSTRACT

A portable dental containment device for use in manipulating dental fixtures, including veneers, in-lays, partials, dentures and other prosthodontics, the device including a transparent enclosure with hand-holes. The dental containment device provides a protected work space in which a dentist, dental assistant, technician, or the like, can manually adjust small fixtures using various hand tools without the risk of ejecting the fixtures, or parts thereof, onto the floor and other unsterile surfaces. The containment device may include autoclavable materials, attachment mechanisms for attaching the shield to a tray, counter top, or other surface, and a magnified viewing area.

11 Claims, 2 Drawing Sheets

DENTAL CONTAINMENT DEVICE

BACKGROUND OF THE INVENTION

The present invention relates to an enclosed work space in which a dentist, or a dental assistant or technician, can physically adjust and manipulate dental fixtures, such as veneers, in-lays, partials, dentures and other prosthodontics, without the risk of dropping, contaminating or losing the fixtures in the process. The dental fixtures are physically small in size, making them especially difficult to secure while adjusting or manipulating and difficult to locate if dropped. It also makes them difficult to see clearly during the process. The fixtures must be re-sterilized each time they come in contact with a non-sterile surface, increasing patient treatment time and reducing operating efficiency. These dental fixtures are also expensive to replace if lost or damaged, usually costing more than $600.00 apiece.

The common method of fitting a dental fixture is to insert it into a patient's mouth to determine preliminarily the physical compatibility of the fixture with the area of the mouth to be treated. The dentist then removes the fixture to make appropriate adjustments for the final fitting. Often, this process requires repeated placements and subsequent adjustments to obtain the ideal fit to the patient's mouth. Due to their small size, fixtures are difficult to see, grasp and manipulate using dental tools. The fixtures frequently slip from tools or the dentist's hands during the adjustment process. This results in the fixtures being lost, damaged or dropped on the floor or other unsterilized surfaces.

OBJECTS AND BRIEF SUMMARY OF THE INVENTION

It is an object of the invention disclosed herein to provide an inexpensive, highly portable, sterile, partially enclosed workspace in which a dentist, or a dental assistant or technician, can conveniently adjust and manipulate dental fixtures.

It is another object of the invention disclosed herein to minimize the risk of dropping a previously sterilized fixture onto the floor or other unsterilized surface during the adjustment process, thereby preventing the need for additional sterilization of the fixture and saving time to fit the fixture to the patient's mouth.

It is another object of the invention disclosed herein to minimize the risk of dropping and losing a fixture, thereby avoiding the expense of having to use another fixture and saving time to fit a new fixture to the patient's mouth.

It is another object of the invention disclosed herein to maximize visibility of a fixture during the adjusting and manipulating process, thereby enhancing the ability to secure the fixture and make appropriate adjustments, as well as promoting efficiency generally.

The invention achieves the above objects by providing a transparent enclosure, defining a protected workspace with hand-holes in the sides. The work space enclosure would be large enough to permit unobstructed use of hands and ordinary dental hand-tools for adjusting and manipulating dental fixtures, including removable and permanent prosthodontics. The hand-holes would come in a variety of sizes to accommodate different hand sizes; the appropriate sized hand-holes would be large enough to enable the unobstructed insertion of the operator's hands and tools, yet small enough to prevent to the fullest extent dental fixtures from falling or otherwise slipping through the excess spaces around the hands.

The containment shield would sit on a horizontal surface in the dental treatment area, such as a tray or countertop, convenient to the dental professional during treatment of a patient. The preferred embodiment of the containment shield would be portable, light weight and would include a base at the bottom of the enclosure that is attachable to the horizontal surface area in order to prevent sliding or upset of the enclosure. The preferred means of attachment would be magnetic or frictional. This would enable the user to move the containment shield easily from one location to another without undue effort mechanically disconnecting it from its present surface. However, the invention contemplates any additional means of attachment to horizontal surfaces, which may include brackets, screws, clamps, clips, suction cups and other means of more permanent fixture. Portability would also enable the invention to be sterilized in an ordinary autoclave.

Embodiments of the invention also include a magnifying surface area to enhance visibility. This magnification would help the dental professional to better manipulate the small dental fixtures while handling them and to more efficiently make adjustments.

BRIEF DESCRIPTION OF THE DRAWINGS

The invention is illustrated in the figures of the accompanying drawings are meant to be exemplary and not limiting.

DETAILED DESCRIPTION OF THE INVENTION

The present invention is directed at preventing time consuming and costly mishaps resulting from adjusting and manipulating dental fixtures. The trimming containment shield described can be conveniently placed on a countertop or a metal tray commonly present in a dentist's treatment facility. The dentist can simply place the subject fixture inside the enclosed work space, insert his or her hands along with the necessary tools through the hand-holes and adjust the fixture while viewing it through the transparent surface areas. Versions of the containment shield include a base that would keep it from sliding across the surface on which it rests. For instance, a magnetic base or a rubber base would keep the containment shield from sliding on a metal tray or countertop.

U.S. Pat. No. 4,108,509 to Piet, et al., entitled "controlled environment work enclosure," discloses an enclosed work-station for use in dental operations to prevent escape of noxious fumes from an amalgamator. This prior art comprises a partially transparent, enclosed workspace with gloved hand-holes through which a dentist may mix amalgam to be used on patients undergoing treatment. The enclosure also includes an exhaust means by which the fumes are directed away from the ambient environment. The design and purpose of the invention, though, is distinguishable from those of the subject dental containment shield. First, the purpose of the controlled environment work enclosure invention was to prevent noxious fumes from entering the treatment area environment. It was not intended or designed to provide a low-cost, convenient method of manipulating dental fixtures without the risk of contamination or loss. Second, the present invention has no provision or need for an exhaust system of any sort as the dental fixtures involved do not emit fumes. Third, the present invention has no provision or need for glove-rings or gloves because the work space enclosure need not be air tight. Furthermore, the gloves would impede the adjustment and manipulation process causing unnecessary delays in "chair-time" treatment of patients.

Figure 1:
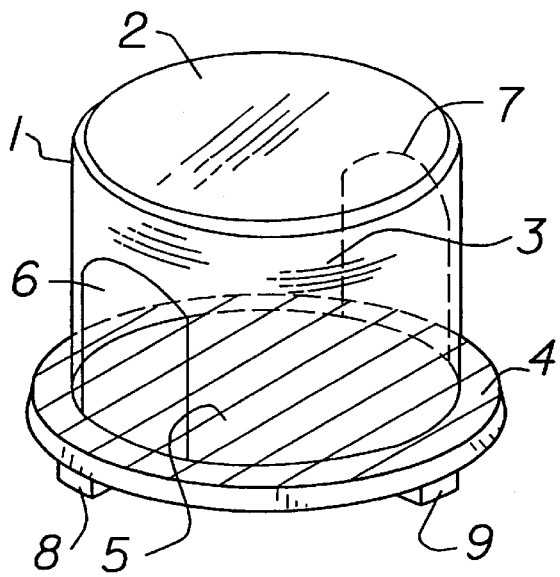
FIG. 1 is a perspective view of one illustrative embodiment of a dental containment shield of the present invention comprising a cylindrical, transparent enclosure with a solid base.
Figure 2:
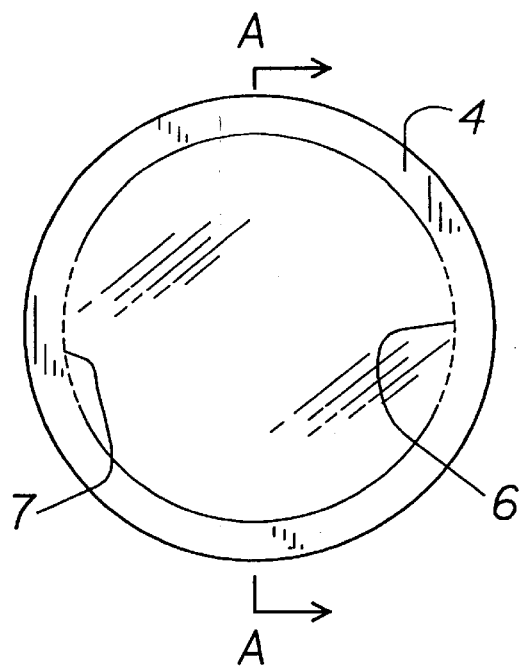
FIG. 2 is a top view of the containment shield in FIG. 1.

Referring to the drawings described above, the trimming containment shield of the present invention comprises interconnected side and top walls 1 and 2 of FIG. 1, respectively, defining a closed chamber or workspace generally designated by the number 3. The preferred embodiment is cylindrical with entirely transparent side and top walls as portrayed by FIG. 1. The dimensions of the preferred embodiment would be 20.3 to 30.5 centimeters (8 to 12 inches) in diameter and 15.2 to 20.3 centimeters (6 to 8 inches) in height, although the invention contemplates any dimensions suitable for a portable work station. The base 4 of FIG. 1 is solid, the top surface 5 of which constitutes the bottom or floor surface of workspace 3.

The preferred dimensions define a workspace large enough to accommodate average-sized human hands working with standard dental hand-tools, yet small enough to promote lightweight, portability, autoclavability and convenience. Autoclavability is a means of sterilizing dental equipment generally, comprising the exposure of items to steam heat of at least 100 degrees centigrade (212 degrees Fahrenheit) for a minimum of 3 minutes at high pressure or 45 minutes at ambient pressure. Autoclavability is critical to the purpose of the invention, as the enclosed workspace does not define an otherwise sterile environment. For example, it is not airtight or sealed against contamination.

The walls of the containment shield may be constructed from a variety of rigid, transparent materials including plastic and glass. Other embodiments of the invention may include non-transparent or opaque walls having sufficient transparent surface space to allow the dentist or dental professional to view the interior of the work space; however, the entirely transparent walls indicated in FIG. 1 are preferable because they enable the best visibility during the adjusting and manipulating process. The base 4 likewise may be constructed from a wide variety of transparent, as well as opaque materials, including plastic, glass, wood, sheet metal, fiber composites and the like, which are suitable as a work surface. All materials however must be autoclavable so that the entire containment shield may be sterilized as appropriate.

Figure 4:
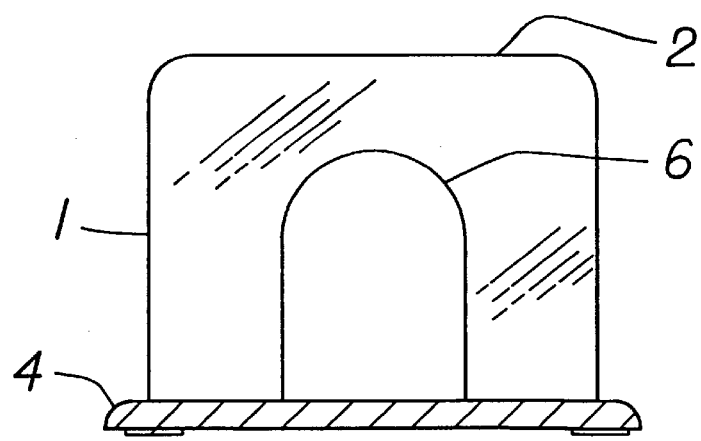
FIG. 4 is an elevation cross-sectional view taken along line a—a of FIG. 2 showing a flat top wall.

The preferred embodiment has two hand-holes 6 and 7, although other embodiments may include additional hand-holes to accommodate additional dental professionals, such as dental assistants and technicians, whose assistance may be needed in work enclosure 7 during the adjusting and manipulating process. The number and dimensions of hand-holes should be minimized to reduce as much as possible the amount of open space through which a dental fixture or prosthesis might be ejected. The dimensions of the hand-holes 6 and 7 contemplated by the preferred embodiment would be 5 to 8 inches high and 5 to 7 inches wide, having an arched top as shown in FIG. 4. The preferred dimensions define hand-holes large enough to accommodate average-sized human hands working with standard dental hand-tools, yet small enough to maximize the open area through which a dental fixture or prosthesis might be ejected.

Figure 3:
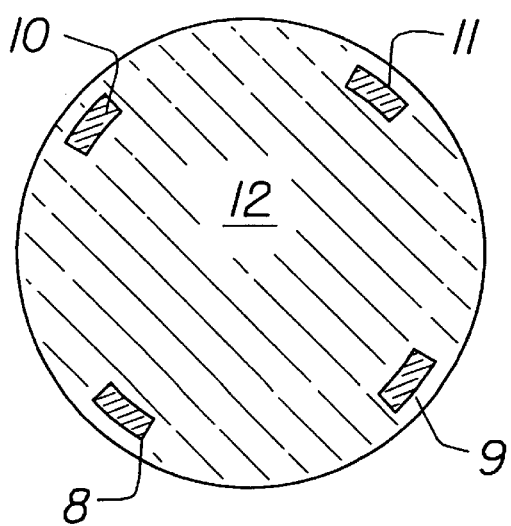
FIG. 3 is a bottom view of the containment shield in FIG. 1.
Figure 3A:
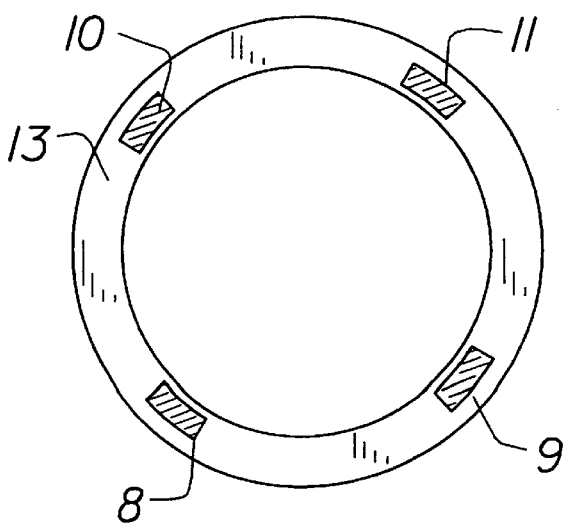
FIG. 3a is a bottom view of the containment shield in FIG. 1, except that FIG. 3a portrays an open, concentric frame base as opposed to the solid, round base portrayed in FIG. 1.

The base 4 of the invention may be a solid surface, as indicated in FIG. 3, or a concentric frame defining the bottom edge of the side walls 1, as indicated in FIG. 3a. The embodiment shown in FIG. 3a would not have a bottom surface or floor internal to the workspace 3. Rather, the operator would incorporate the surface on which the containment shield sits, such as a metal tray or countertop, as the bottom of the workspace.

Whether the base 4 is solid as in FIG. 3 or open as in FIG. 3a, the preferred embodiment of the invention contains means by which to secure the containment shield to the horizontal surface on which it sits. These means can be magnetic, frictional or mechanical in nature. The figures incorporated herein show attachment means 8, 9, 10 and 11 of FIGS. 1, 3 and 3a. The attachment means pictured are strips of magnet connected to the bottom of the base, which would secure the containment shield to metal surfaces such as trays and countertops commonly present in treatment areas of dental facilities. The attachment means may also be frictional; for example it may consist of strips of soft rubber, granulated plastic or any other material having a high coefficient of static friction that prevents or reduces lateral slippage on smooth surfaces. The frictional attachment means may be enhanced through a weighted base. The mechanical means of attachment includes any means of physically connecting the base 4 to an available mount in a patient treatment area, including brackets, screws, clamps, clips, suction cups and glue. These mechanical connections make the containment shield more secure and less likely to slip during the adjusting or manipulating process, although it may render the containment shield less portable, as well as less convenient to autoclave. The invention contemplates attachment means of any shape, size and number; for example, the entire bottom surface 12 of FIG. 3 may be a magnetized or rubber surface.

Figure 4A:
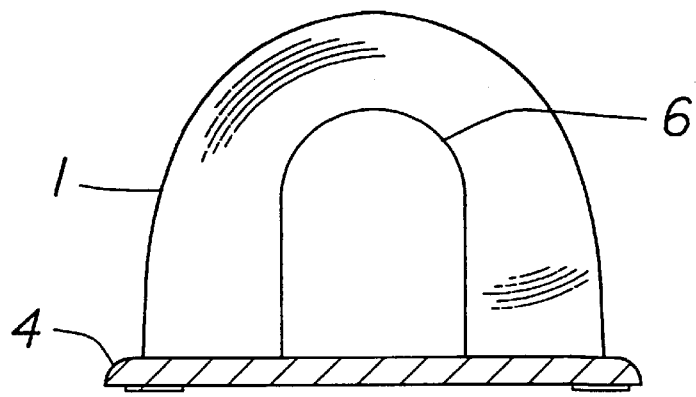
FIG. 4a is an elevation cross-sectional view taken along line a—a of FIG. 2 showing a convex combination of side and top walls.
Figure 5:
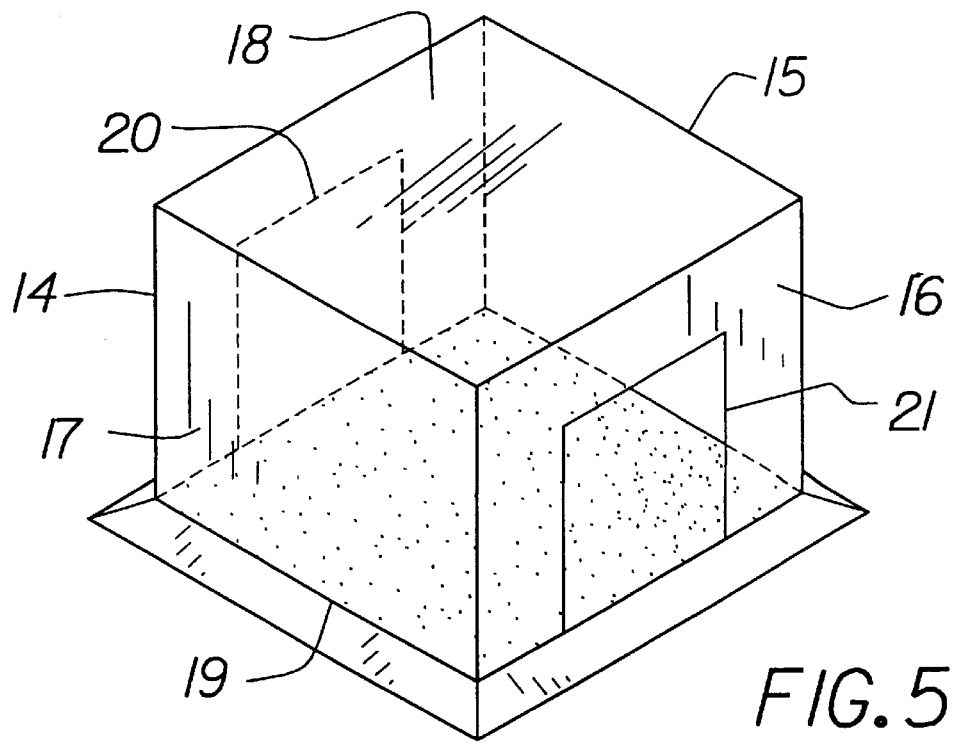
FIG. 5 is a perspective view of another illustrative embodiment of a dental containment shield of the present invention comprising a square rather than cylindrical enclosure, base and hand-holes.

Embodiments of the invention include any shape of workspace enclosure, base and hand-holes. As examples, FIG. 4a portrays a cylindrical enclosure having a generally convex shape essentially merging the side and top walls and FIG. 5 portrays a generally square-shaped enclosure having four vertical side walls 14, 15, 16 and 17, a square top surface 18, a square base 19 and rectangular hand-holes 20 and 21. The basic function of invention remains the same, which is to provide generally a transparent work enclosure in which a dentist, dental assistant or technician, can adjust manually small dental fixtures, including the use of standard hand-tools, without losing the fixtures or dropping them onto unsterile surfaces.

Embodiments of the invention also include a magnifying portion of a transparent wall, either side or top. This magnifying portion would enable the dental professional to view the fixture being adjusted and manipulated in an enhanced fashion, making said adjustments and manipulations easier and more efficient. The preferred embodiment of the magnifying containment shield would contain a magnified portion large enough for practical use, yet small enough to allow unmagnified viewing of the object, as desired, by the operator's altering his or her line of sight.

What is claimed is:

1. A dental containment device used in performance of manipulations of a dental fixture comprising:

a shield portion defining an interior work space and at least two unobstructed openings that enable simultaneous insertion of an operator's hands into the interior work space, together with at least one of a dental tool and the dental fixture, without creating an airtight seal around the operator's hands; and at least one transparent surface area that provides the operator an unobstructed view into the interior work space;

wherein the operator's hands can manipulate the dental fixture within the interior work space while being observed through the at least one transparent surface area.

2. The dental containment device according to claim 1, further comprising:

at least one attachment mechanism that secures said shield portion to an exterior surface.

3. The dental containment device according to claim 1, each of the at least two openings being positioned diametrically opposed to one another.

4. The dental containment device according to claim 1, said shield portion comprising an autoclavable material capable of withstanding a sterilization process.

5. The dental containment device according to claim 1, the at least one transparent surface area comprising a magnifying viewing portion.

6. A dental containment device used in a performance of manipulation of a dental fixture comprising:

a shield portion defining an interior work space and two unobstructed openings, each of the two openings having a dimension and being positioned to enable an unimpeded insertion of a hand into the interior work space, together with at least one of a dental tool and the dental fixture, with sufficient clearance to permit the manipulation of the dental fixture; and a transparent surface area that provides an unobstructed view into the interior work space.

7. The dental containment device according to claim 6, wherein the dimension and the position of each of the two openings is configured for one hand to be inserted though each opening.

8. The dental containment device according to claim 6, further comprising:

at least one attachment mechanism that attaches the dental containment device to an exterior surface.

9. The dental containment device according to claim 6, said shield portion comprising a material capable of withstanding an autoclaving process.

10. The dental containment device according to claim 6, the at least one transparent surface area comprising a magnifying viewing portion.

11. A dental containment device used in a performance of manipulation to a dental fixture comprising:

a shield portion defining an interior work space and two unobstructed openings, each of the two openings having a dimension and being positioned to enable an unimpeded insertion of a hand into the interior work space, together with at least one of a dental tool and the dental fixture, with sufficient clearance to permit the manipulation of the dental fixture, said shield portion comprising an autoclavable material;

a transparent surface area that provides an unobstructed view into the interior work space; and at least one attachment mechanism that attaches the dental containment device to an exterior surface.

* * * * *